(12) United States Patent
Burgmaier et al.

(10) Patent No.: US 6,506,934 B1
(45) Date of Patent: Jan. 14, 2003

(54) WATER SOLUBLE HALOGEN-CONTAINING COMPOUNDS

(75) Inventors: George J. Burgmaier, Pittsford, NY (US); Roger L. Klaus, Victor, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/014,223

(22) Filed: Dec. 11, 2001

(51) Int. Cl.⁷ .................. C07C 315/00; C07F 9/22
(52) U.S. Cl. ............ 562/556; 562/11; 562/426; 564/15; 564/162; 558/61; 558/30
(58) Field of Search .......... 562/11, 556, 426; 564/15, 162; 558/61, 30

(56) References Cited

U.S. PATENT DOCUMENTS 3,946,007 A 3/1976 Goralski et al.

OTHER PUBLICATIONS

Jarvia et al, J. Org. Chem., vol. 40 (25), 1975.*
Hans Pritzkow et al, Darstellung perhalogenierter Mesyl-sulfene, $X_3C-SO_2-C(X)=SO_2$, und ihre Stabilisierung durch Chinuchlidin, Feb. 1990, pp. 1187–1192.
Bruce B. Jarvis et al. J. Org. Chem., vol. 40, No. 25, 1975, pp. 3778–3780.
Dieter Scholz, Neue Synthesemethoden, 10, Liebigs Ann. Chem., 1984, pp. 264–272.
Udo Rheude et al, "Uber Reaktionen halogenierter Methansulfonylchloride mit Trimethylamin und ein inverses Sulfen–Amin–Addukt", Chem. Ber. 118, 1985, pp. 2208–2219.
George J. Burgmaier et al U.S. application Ser. No. 10/014961"Photothermographic Materials Containing Solubilized Antifoggants" (Docket 81832/JLT).
Roger L. Klaus et al U.S. application Ser. No. 10/014990 "Silver Halide Photographic Materials Containing Solubilized Antifoggants" (Docket 82700/SMR).
Kenneth J. Reed et al U.S. application Ser. No. 10/014709 "Silver Halide Elements Containing Solubilized Antifoggants and Low Fogging Tabular Silver Halide Grains" (Docket 82988/SMR).

* cited by examiner

*Primary Examiner*—Alan L. Rotman
*Assistant Examiner*—Hector M Reyes
(74) *Attorney, Agent, or Firm*—Sarah Meeks Roberts

(57) ABSTRACT

This invention relates to a compound that is represented by the following Structure I:

$$R_1-SO_2-C(R_2)R_3-(CO)_m-(L)_n-SG \qquad I$$

wherein $R_1$ is an aliphatic or cyclic group, $R_2$ and $R_3$ are independently hydrogen or bromine as long as at least one of them is bromine, L is an divalent linking group, m and n are independently 0 or 1, SG is a solubilizing group with a pKa of 8 or less, with the proviso that when m and n are both 0, SG is not a sulfo (or salt thereof) or a sulfonamido (or salt thereof) and when m is 0 and n is 1, either L is not an alkylene group or SG is not a carboxy (or salt thereof).

13 Claims, No Drawings

WATER SOLUBLE HALOGEN-CONTAINING COMPOUNDS

FIELD OF THE INVENTION

This invention relates to certain water soluble halogen-containing compounds and the preparation of said compounds. These compounds are particularly useful as antifoggants in silver halide photographic materials. These compounds are also useful as water-soluble reagents useful for the bromination of organic chemicals. It is also anticipated that these compounds may be useful as water-soluble oxidants and water-soluble antimicrobial agents.

BACKGROUND OF THE INVENTION

Problems with fogging have plagued the photographic industry from its inception. Fog is a deposit of silver or dye that is not directly related to the image-forming exposure, i.e., when a developer acts upon an emulsion layer, some reduced silver is formed in areas that have not been exposed to light. Fog can be defined as a developed density that is not associated with the action of the image-forming exposure, and is usually expressed as "D-min", the density obtained in the unexposed portions of the emulsion. Density, as normally measured, includes both that produced by fog and that produced as a function of exposure to light. It is known in the art that the appearance of photographic fog related to intentional or unintentional reduction of silver ion (reduction sensitization) can occur during many stages of preparation of the photographic element including silver halide emulsion preparation, spectral/chemical sensitization of the silver halide emulsion, melting and holding of the liquid silver halide emulsion melts, subsequent coating of silver halide emulsions, and prolonged natural and artificial aging of coated silver halide emulsions. The chemicals used for preventing fog growth as a result of aging or storage are generally known as emulsion stabilizers.

The control of fog, whether occurring during the formation of the light-sensitive silver halide emulsion, during the spectral/chemical sensitization of those emulsions, during the preparation of silver halide compositions prior to coating on an appropriate support, or during the aging of such coated silver halide compositions, has been attempted by a variety of means. Mercury-containing compounds, such as those described in U.S. Pat. Nos. 2,728,663; 2,728,664; and 2,728,665, have been used as additives to control fog. Thiosulfonates and thiosulfonate esters, such as those described in U.S. Pat. Nos. 2,440,206; 2,934,198; 3,047,393; and 4,960,689, have also been employed. Organic dichalcogenides, for example, the disulfide compounds described in U.S. Pat. Nos. 1,962,133; 2,465,149; 2,756,145; 2,935,404; 3,184,313; 3,318,701; 3,409,437; 3,447,925; 4,243,748; 4,463,082; and 4,788,132 have been used not only to prevent formation of fog, but also as desensitizers and as agents in processing baths and as additives in diffusion transfer systems.

However, despite all the efforts in this field there still remains a need for compounds which act as effective antifoggants in photographic elements which are stored under high temperature conditions. There is particularly a need for antifoggants which are water soluble and thus are safer to utilize during manufacture of the photographic elements.

In addition, a problem which has faced synthetic organic chemist is the availability of a reagent for brominating organic chemicals that can be handled safely and is stable when dissolved in water, i.e. a brominating reagent that does not react with water when it is dissolved in water. Molecular bromine is a useful brominating agent but it is not very soluble in water and the toxic liquid is often difficult to handle. Other brominating agents such as the commercially available 1,3-dibromo-5,5-dimethylhydantoin are sometimes sensitive to moisture.

SUMMARY OF THE INVENTION

This invention provides compounds represented by the following Structure I:

$$R_1—SO_2—C(R_2)R_3—(CO)_m—(L)_n—SG \qquad I$$

wherein $R_1$ is an aliphatic or cyclic group, $R_2$ and $R_3$ are independently hydrogen or bromine as long as at least one of them is bromine, L is a divalent linking group, m and n are independently 0 or 1, SG is a solubilizing group with a pKa of 8 or less, with the proviso that when m and n are both 0, SG is not a sulfo (or salt thereof) or a sulfonamido (or salt thereof and when m and n are both 1, either L is not an alkylene group or SG is not a carboxy (or salt thereof).

The compounds of this invention reduce fogging during chemical sensitization of silver halide photographic elements. They further enhance fog retardation of liquid emulsions during high temperature holding. The water soluble antifoggants minimize the need for expensive and time-consuming preparation of solid-particle dispersions, as well as minimize the need for volatile organic solvents. Use of these materials also eliminates the need to use environmentally undesirable heavy metal antifoggant salts such as mercuric salts. It is also believed that these compounds may have utility as antifoggants and stabilizers for thermographic and photothermographic elements. They may also be useful as brominating agents in the preparation of pharmaceutical compounds and other organic chemicals. Additionally these compounds may be useful as water soluble oxidants and as water soluble antimicrobial agents. These and other advantages will be apparent from the detailed description below.

DETAILED DESCRIPTION OF THE INVENTION

The compounds of this invention are water-soluble or water-dispersible compounds represented by the following Structure I:

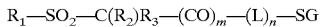

$$R_1—SO_2—C(R_2)R_3—(CO)_m—(L)_n—SG \qquad I$$

wherein $R_1$ is a substituted or unsubstituted aliphatic or cyclic group of any size as long as the antifoggant remains soluble or readily dispersible in water. Substituted or unsubstituted aliphatic groups for $R_1$ include monovalent groups having 1 to 20 carbon, nitrogen, sulfur, and oxygen atoms in the chain including, but not limited to, chains that include one or more substituted or unsubstituted alkyl groups having 1 to 10 carbon atoms, substituted or unsubstituted alkenylene groups having 2 to 20 carbon atoms, substituted or unsubstituted alkylenearylene groups having 7 to 20 carbon atoms in the chain, and combinations of any of these groups, as well as combinations of these groups that are connected with one or more amino, amido, carbonyl, sulfonyl, carbonamido, sulfonamido, thio, oxy, oxycarbonyl, oxysulfonyl, and other connecting groups that would be readily apparent to one skilled in the art. The various types of useful aliphatic groups would be readily apparent to one skilled in the art. Preferred aliphatic groups for $R_1$ include substituted or unsubstituted t-butyl groups and trifluoromethyl groups.

$R_1$ can also be substituted or unsubstituted cyclic groups including substituted or unsubstituted carbocyclic aryl groups having 6 to 14 carbon atoms to form the cyclic ring, substituted or unsubstituted cycloalkylene groups (having 5 to 10 carbon atoms to form the cyclic ring) and heterocyclic groups (having 5 to 10 carbon, nitrogen, sulfur, or oxygen atoms to form the cyclic ring), both aromatic and non-aromatic. The various types of cyclic groups would be readily apparent to one skilled in the art.

Preferred cyclic groups for $R_1$ include substituted or unsubstituted aryl groups having 6 to 10 carbon atoms to form the cyclic ring. Substituted or unsubstituted phenyl groups are most preferred. Methyl groups are preferred substituents on the phenyl group.

In Structure I, $R_2$ and $R_3$ are independently hydrogen or bromine as long as one of them is bromine. Preferably, both $R_2$ and $R_3$ are bromine.

In addition, L is a substituted or unsubstituted divalent linking group, and more preferably an aliphatic linking group that can have the same definition as $R_1$ except that L is divalent. Thus, one skilled in the art would be able to determine suitable L groups that would serve the desired purpose while maintaining compound water solubility or dispersibility. Preferably, L is —NH-alkylene wherein "alkylene" is substituted or unsubstituted and has 1 to 10 carbon atoms (more preferably 1 to 3 carbon atoms).

Substituents on $R_1$ and L can be any chemical moiety that would not adversely affect the desired function of the antifoggant and can include, but are not limited to, alkyl, aryl, heterocyclic, cycloalkyl, amino, carboxy, hydroxy, phospho, sulfonamido, sulfo, halo and other groups that would be readily apparent to one skilled in the art. The number of substituents is limited only by the number of available valences (available hydrogen atoms). Alkyl groups are preferred substituents for cyclic $R_1$ groups. However, as would be apparent, the antifoggants can have multiple sulfo, carboxy, phospho, and sulfonamido groups that impart water solubility to the molecule. Further, in Structure I, m and n are independently 0 or 1, and preferably, both are 1.

SG can be any suitable solubilizing group which has a pKa of 8 or less and which does not interfere with the antifogging activity of the compound. SG may be in the free acid form or it may be a salt, particularly a suitable metal (for example, alkali metal salt) or ammonium ion salt. Preferably, SG is a salt. When SG is in its free acid form, the salt can be generated in situ by neutralization with any basic material commonly used by one skilled in the art. Preferably SG is a carboxy, phospho, sulfo or sulfonamido group. When SG is a sulfonamido group, it may be —$SO_2N^-COR_4M^+$, or —$NSO_2R_4M^+$ with $R_4$ being a substituted or unsubstituted aliphatic or cyclic group that is defined the same as for $R_1$, although $R_1$ and $R_4$ can be the same or different in a particular compound. Preferably, SG is a carboxy or sulfo group (or salts thereof), particularly when both m and n are 1. However, when m and n are both 0, SG is not a sulfo (or salt thereof) or a sulfonamido (or salt thereof) and when m is 0 and n is 1, either L is not an alkylene group or SG is not a carboxy (or salt thereof). In one embodiment when m and n are both 0, SG is a carboxy (or salt thereof) or phospho (or salt thereof). In another embodiment when m is 0, n is 1 and L is an alkylene group, SG is sulfo (or salt thereof), phospho (or salt thereof), or sulfonarnido (or salt thereof).

$M^+$ is a suitable cation such as a metal cation (preferably alkali metal ion) or an ammonium ion. When $M^+$ is a hydrogen atom the resulting free acid can be easily solubilized by neutralization with any convenient base, such as, for example, potassium hydroxide or sodium bicarbonate.

Representative antifoggants useful within the practice of this invention include the following compounds:

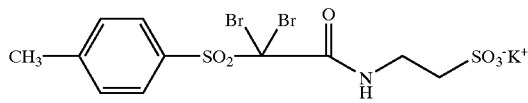

A-1

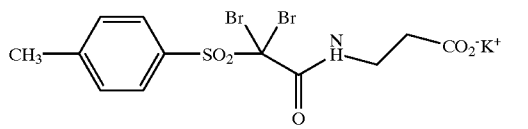

A-2

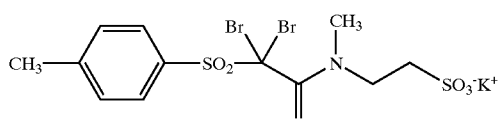

A-3

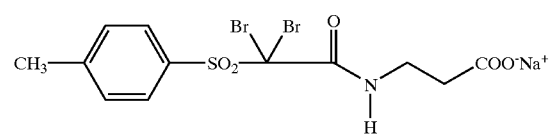

A-4

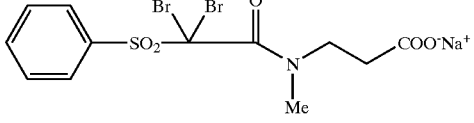

A-5

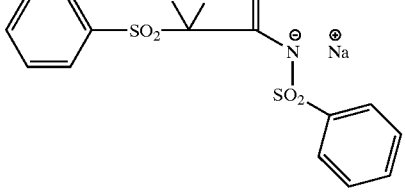

A-6

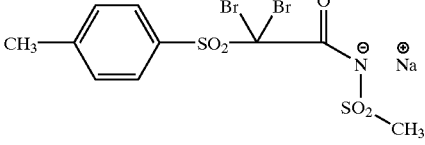

A-7

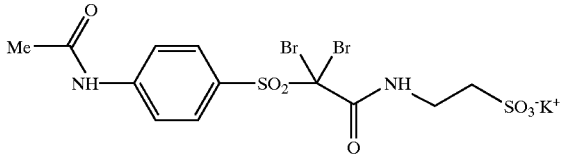

A-8

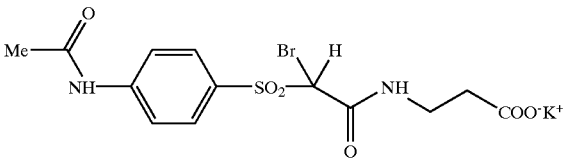

A-9

The compounds represented by Structure I can be prepared using starting materials and procedures that would be readily apparent to one skilled in the art. For example, compounds wherein m is 1 (and n is 0 or 1) can be prepared by reacting a salt of a sulfinic acid (such as p-toluenesulfinic acid, sodium salt) with a 2-bromomethylcarbonyl derivative, followed by bromination of the resulting sulfone using molecular bromine or another suitable brominating agent.

Instead of using the salt of a sulfinic acid, an aromatic or aliphatic thiol can be condensed with the 2-bromomethylcarbonyl derivative followed by oxidation of the thioether to a sulfone and then subsequent bromination.

Some 2-bromomethylcarbonyl derivatives can be prepared by reacting bromoacetylbromide with amines such as taurine, as described in U.S. Pat. No. 5,091,298 (Parton et al), with glycine, as described in the Journal of the Korean Society of Textile Engineers and Chemists, p 13, December 1981 (Hwang et al), or with methanesulfonamide, as described in U.S. Pat. No. 5,620,989 (Harrison et al).

Monobromination can be achieved by using only one equivalent of a source of bromine, using a less active brominating agent, or by adjusting reaction conditions as one skilled in the art would readily understand. A useful reagent capable of being a water-soluble brominating agent is the inventive compound represented by structure 1. For example, when one mole of inventive antifoggant A-1 is added to an alkaline solution of the unbrominated precursor of A-1, two moles of inventive antifoggant A-20 are formed almost instantaneously at room temperature. This reaction also occurs at lower pH, but more slowly. The use of the water-soluble inventive antifoggant A-1 as a brominating agent produces one mole of the water soluble inventive antifoggant A-20 as a reaction product. This is particularly helpful when the isolation and purification of a water-insoluble bromination product is desired. This will be exemplified later for the preparation of inventive antifoggant A-24.

By "water-soluble" or "water-dispersible" in defining the antifoggants is meant that the compounds are readily dissolved or dispersed in water. Therefore, their use in silver halide emulsions and photographic elements alleviates the need for volatile organic solvents and circumvents the disadvantages of using solid particle dispersions. In order to be "water-soluble" or "water-dispersible", it should be possible to add between 0.1 g and 500 g of the antifoggant to 1000 mL of water. Optimally, it should be possible to add between 50 g and 200 g of the antifoggant to 1000 mL of water. The antifoggants can be used individually or in combination in the elements of this invention. Generally, they are present in an amount of at least 0.0001 mol/mol of total silver. Preferably, they are present in an amount of from about 0.001 to about 0.1 mol/mol of total silver.

The antifoggant compounds may be added to any layer where they are in reactive association with the silver halide. By "in reactive association with" it is meant that the compounds must be contained in the silver halide emulsion layer or in a layer whereby they can react or interact with, or come in contact with, the silver halide emulsion. Preferably, the antifoggants are included in the one or more emulsion layers, but during manufacture, they can also be incorporated into interlayers, underlayers, and protective topcoat layers on the frontside of the support. If they are placed in a non-emulsion layer, they tend to migrate into the emulsion layer(s) where they become effective in reducing $D_{min}$. The antifoggant compounds may be added to the photographic emulsion using any technique suitable for this purpose.

Photographic emulsions are generally prepared by precipitating silver halide crystals in a colloidal matrix by methods conventional in the art. The colloid is typically a hydrophilic film forming agent such as gelatin, alginic acid, or derivatives thereof.

The crystals formed in the precipitation step are washed and then chemically and spectrally sensitized by adding spectral sensitizing dyes and chemical sensitizers, and by providing a heating step during which the emulsion temperature is raised, typically from 40° C. to 70° C., and maintained for a period of time. The precipitation and spectral and chemical sensitization methods utilized in preparing the emulsions employed in the invention can be those methods known in the art.

Chemical sensitization of the emulsion typically employs sensitizers such as: sulfur-containing compounds, e.g., allyl isothiocyanate, sodium thiosulfate and allyl thiourea; reducing agents, e.g., polyamines and stannous salts, noble metal compounds, e.g., gold, platinum, and polymeric agents, e.g., polyalkylene oxides. As described, heat treatment is employed to complete chemical sensitization. Spectral sensitization is effected with a combination of dyes, which are designed for the wavelength range of interest within the visible or infrared spectrum. It is known to add such dyes both before and after heat treatment.

After spectral sensitization, the emulsion is coated on a support. Various coating techniques include dip coating, air knife coating, curtain coating and extrusion coating.

The antifoggants may be added to the silver halide emulsion at any time during the preparation of the emulsion, i.e., during precipitation, during or before chemical sensitization or during final melting and co-mixing of the emulsions and additives for coating. More preferably these compounds are added after precipitation and washing and most preferably during or directly after chemical sensitization of the final melt.

The compounds of the invention may be used in black and white elements, single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, and subbing layers.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire PO10 7DQ, ENGLAND, the contents of which are incorporated herein by reference. Further, the photographic elements may have an annealed polyethylene naphthalate film base such as described in Hatsumei Kyoukai Koukai Gihou No. 94-6023, published Mar. 15, 1994 (Patent Office of Japan and Library of Congress of Japan) and may be utilized in a small format system, such as described in *Research Disclosure*, June 1994, Item 36230 published by Kenneth Mason Publications, Ltd., Dudley Annex, 12a North Street, Emsworth, Hampshire PO10 7DQ, ENGLAND, and such as the Advanced Photo System, particularly the Kodak ADVANTIX films or cameras.

In the following Table, reference will be made to (1) *Research Disclosure*, December 1978, Item 17643, (2) *Research Disclosure*, December 1989, Item 308119, (3) *Research Disclosure*, September 1994, Item 36544, and (4) *Research Disclosure*, September 1996, Item 38957, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the elements of the invention. The Table and its cited references also describe suitable ways of preparing, exposing, processing and manipulating the elements, and the images contained therein. Photographic elements and methods of processing such elements particularly suitable for use with this invention are described in *Research Disclosure*, February 1995, Item 37038, published by Kenneth Mason Publications, Ltd., Dudley Annex, 12a North Street, Emsworth, Hampshire PO10 7DQ, ENGLAND, the disclosure of which is incorporated herein by reference.

| Reference | Section | Subject Matter |
| --- | --- | --- |
| 1 | I, II | Grain composition, morphology and preparation. Emulsion preparation including hardeners, coating aids, addenda, etc. |
| 2 | I, II, IX, X, XI, XII, XIV, XV | |
| 3 & 4 | I, II III, IX A & B | |
| 1 | III, IV | Chemical sensitization and spectral sensitization/ desensitization |
| 2 | III, IV | |
| 3 & 4 | IV, V | |
| 1 | V | UV dyes, optical brighteners, luminescent dyes |
| 2 | V | |
| 3 & 4 | VI | |
| 1 | VI | Antifoggants and stabilizers |
| 2 | VI | |
| 3 & 4 | VII | |
| 1 | VIII | Absorbing and scattering materials; Antistatic layers; matting agents |
| 2 | VIII, XIII, XVI | |
| 3 & 4 | VIII, IX C & D | |
| 1 | VII | Image-couplers and image-modifying couplers; Wash-out couplers; Dye stabilizers and hue modifiers |
| 2 | VII | |
| 3 & 4 | X | |
| 1 | XVII | Supports |
| 2 | XVII | |
| 3 & 4 | XV | |
| 3 & 4 | XI | Specific layer arrangements |
| 3 & 4 | XII, XIII | Negative working emulsions; Direct positive emulsions |
| 2 | XVIII | Exposure |
| 3 & 4 | XVI | |
| 1 | XIX, XX | Chemical processing; Developing agents |
| 2 | XIX, XX, XXII | |
| 3 & 4 | XVIII, XIX, XX | |
| 3 & 4 | XIV | Scanning and digital processing procedures |

The photographic elements can be incorporated into exposure structures intended for repeated use or exposure structures intended for limited use, variously referred to as single use cameras, lens with film, or photosensitive material package units.

The following examples are intended to illustrate, but not to limit, the invention:

EXAMPLES

Example 1

Inventive antifoggant A-1

Antifoggant A-1 is 2,2'-dibromo-(4-methylphenyl) sulfonyl-N-(2-sulfoethyl) acetamide potassium salt, and has the structure shown above. Compound A-1 was prepared as follows:

To a 5-liter flask equipped with a mechanical stirrer and reflux condenser was addedp-toluenesulfinic acid, lithium salt (308.57 g), N-(2-sulfoethyl)-2-bromoacetamide, lithium salt (527.39 g), water (180 ml), and ethyl alcohol (3380 ml). The resulting suspension was heated to reflux. After about an hour of reflux, nearly all of the reactants had dissolved. Reflux was continued another four hours, and the solution was filtered hot through a Celite pad to remove some haziness. The solution was cooled overnight to room temperature. The solid that formed was collected and washed with 1 liter of 95% ethyl alcohol/water. The white solid was air-dried and then dried at high vacuum, providing 553.88 g (89% yield) of 2-(4-methylphenyl)sulfonyl-N-(2-sulfoethyl) acetamide, lithium salt (Intermediate 1). HPLC analysis showed no detectable impurities. Ion chromatography indicated 0.035 weight % bromide and 1.8 weight % lithium. The material exhibited an acceptable proton spectrum.

To glacial acetic acid (660 ml) was added Intermediate 1 (98.19 g), and 1,3-dibromo-5,5-dimethylhydantoin (42.89 g). The resulting suspension was heated to reflux where solution occurred. After about 3–5 minutes at reflux, the slight bromine color was discharged, and reflux was continued to. another 15 minutes. Analysis of the reaction mixture by HPLC indicated conversion to one main product. After cooling to near room temperature, most of the acetic acid was removed on the rotary film evaporator using a water aspirator (water bath temperature at 40° C.) The residue was diluted with 2500 ml of ethyl alcohol. Complete solution occurred after stirring the suspension for one hour at room temperature. To this stirring solution at room temperature was added dropwise a solution of potassium acetate (58.88 g) dissolved in ethyl alcohol (500 ml). A white solid formed immediately. Upon complete addition of the potassium acetate solution, the suspension was stirred at room temperature for 90 minutes, and the desired antifoggant A-1, 2,2-dibromo-2-(4-methylphenyl)sulfonyl-N-(2-sulfoethyl) acetarnide, potassium salt, was collected by filtration and washed with ethyl alcohol. The solid was then dried under high vacuum at 40° C. The yield of crude antifoggant A-1, which had a slight odor of acetic acid, was 145.22 g (94%).

Two separate synthetic batches of A-1 were made, combined, and recrystallized by dissolving 182.33 g of product in a mixture of water (85 ml) and ethyl alcohol (600 ml) while boiled, filtered hot, and adding about 7 ml water upon cooling to prevent oiling. After letting the solution stand overnight at room temperature, the desired antifoggant product was collected and washed with about 300 ml (10:1 v/v) ethyl alcohol/water mixture. The product was then air-dried and then dried under high vacuum at 40° C., providing 159.87 g of desired product. HPLC analysis indicated an assay of 99.2% of the desired component. The product exhibited the expected proton nmr spectrum and mass spectrum consistent with the A-1 structure shown above.

Example 2

Inventive Antifoggant A-2

Inventive antifoggant A-2 is 2,2'-dibromo-(4-methylphenyl) sulfonyl-N-(2-carboxyethyl)acetamide, potassium salt, and has the structure noted above. Compound A-2 was prepared similarly to Compound A-1 except that the N-(2-sulfoethyl)-2-bromoacetamide, lithium salt is replaced by the HCl salt of the ethyl ester of β-alanine. The resulting substituted bromoacetamide is reacted as above with the sodium salt of toluenesufinic acid followed by alkaline hydrolysis of the ester and subsequent reaction with bromine to form A-2.

Example 3

Inventive Antifoggant A-7

Inventive antifoggant A-7 was prepared similarly to Compound A-1 except that N-bromoacetylmethanesulfonamide was reacted with the sodium salt of toluenesulfinic acid in 95/5 ethanol/water (v/v) at reflux for 5 hr, isolating Intermediate 2. Intermediate 2 was further purified by a recrystallization from 90/10 (v/v) ethanol/water. Intermediate 2 was then brominated with two moles of molecular bromine in refluxing acetic acid containing two moles of sodium acetate. A small amount of insoluble material was removed by filtration after cooling the reaction mixture to room temperature, and the filtrate was concentrated and diluted with water, isolating antifoggant A-7. The crude product was further purified by a recrystallization from 80/20 (v/v) methanol/water.

Example 4

Inventive Antifoggant A-20

Method One

Inventive antifoggant A-20 is 2-bromo-2-(4-methylphenyl) sulfonyl-N-(2-sulfoethyl)acetamide lithium salt, and has the structure drawn above. Compound A-20 was prepared as follows: To glacial acetic acid (125 ml) was added Intermediate 1 (18.66 g), and the suspension was heated in an oil bath at a temperature of 52° C. To the stirring suspension was added dropwise over a 5 hr period a solution of bromine (14.77 g) dissolved in glacial acetic acid (15 ml). Upon complete addition, the temperature of the oil bath was maintained at 52° C. for 75 min., and then the heat was removed. Upon standing at room temperature, solid formed. The product was collected and washed sequentially with glacial acetic acid and acetonitrile and dried in a vacuum oven, obtaining 20.21 g of a white solid. The material was further purified by dissolving the solid (17.30 g) at the boil in 200 ml acetonitrile containing 4 ml water, and then cooling to room temperature. Examination by HPLC indicated greater than 99% of one component that analyzed by both mass spectroscopy and NMR for A-20, 2-bromo-2-(4-methylphenyl)sulfonyl-N-(2-sulfoethyl) acetamide lithium salt.

Method Two

To a solution containing 1 mmol of Intermediate 1 in about 1 mL of water was added a solution of 1 mmol of inventive antifoggant A-1 also in about 1 mL of water. To this solution at room temperature was added 2 mL of a 0.1 M sodium hydroxide solution. Analysis of this solution by HPLC after 5 minutes indicated the nearly complete absence of starting materials and complete conversion to the material corresponding to that prepared by Method One.

Example 5

Inventive Antifoggant A-24

Inventive antifoggant A-24 was prepared using Inventive antifoggant A-1 as a convenient water-soluble brominating reagent. A solution of 0.92 g of sodium hydroxide and 2.91 g (10 mmol) of Intermediate 2 in 32 mL water was prepared. To this solution at room temperature was added dropwise a solution of 5.17 g (10 mmol) of antifoggant A-1 dissolved in 10 mL water. Upon complete addition, the solution was allowed to stir at room temperature for 5 min. Analysis of the reaction mixture by HPLC indicated the presence of the water-soluble mono-bromo inventive antifoggant A-20 as well as one other main component. A solution of 2 mL conc HCl in 20 mL water was added. A semi-solid separated which was further purified by dissolving the semi-solid in ethyl acetate and washing the organic phase with water, concentrating the ethyl acetate to give 3.52 g (95% yield) of a white solid. The product was further purified by a recrystallization from 50/50 (v/v) aqueous ethanol, to yield a material for which HPLC analysis indicated 98 area % one component. The product had a proton and mass spectrum corresponding to protonated form of antifoggant A-24.

The invention has been described in detail with particular reference to certain preferred embodiments thereof, but it will be understood that variations and modifications can be effected within the spirit and scope of the invention.

What is claimed is:

1. A compound that is represented by the following Structure I:

$$R_1-SO_2-C(R_2)R_3-(CO)_m-(L)_n-SG \qquad I$$

wherein $R_1$ is an aliphatic or cyclic group, $R_2$ and $R_3$ are independently hydrogen or bromine as long as at least one of them is bromine, L is an divalent linking group, m and n are independently 0 or 1, SG is a solubilizing group with a pKa of 8 or less, with the proviso that when m and n are both 0, SG is not a sulfo (or salt thereof) or a sulfonamido (or salt thereof) and when m is 0 and n is 1, either L is not an alkylene group or SG is not a carboxy (or salt thereof).

2. The compound of claim 1 wherein said SG is a sulfo, phospho, sulfonamido or carboxy group, or salt thereof.

3. The compound of claim 1 wherein said SG is a sulfo or carboxy group, or salt thereof.

4. The compound of claim 1 wherein both $R_2$ and $R_3$ are bromine.

5. The compound of claim 1 wherein $R_1$ is a substituted or unsubstituted t-butyl, trifluoromethyl, or phenyl group.

6. The compound.of claim 1 wherein m and n are each 1.

7. The compound of claim 1 wherein m and n are both 0.

8. The compound of claim 1 wherein m is 1 and n is 0.

9. The compound of claim 1 wherein m is 0 and n is 1.

10. The compound of claim 1 wherein n is 1 and L is a substituted or unsubstituted —NH-alkylene-group.

11. The compound of claim 1 wherein L is an aliphatic linking group.

12. The compound of claim 1 wherein:

when m and n are both 0, SG is carboxy (or salt thereof), phospho (or salt thereof), or sulfonamido (or salt thereof), and when m is 0, n is 1 and L is an alkylene group, SG is sulfo (or salt thereof), phospho (or salt thereof), sulfonamido (or salt thereof).

13. The compound of claim 1 wherein said compound is one or more of the following compounds A-1 to A-28:

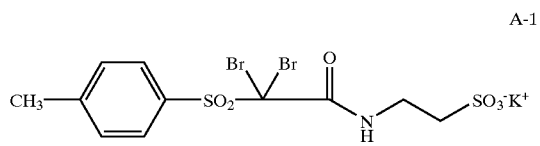

A-1

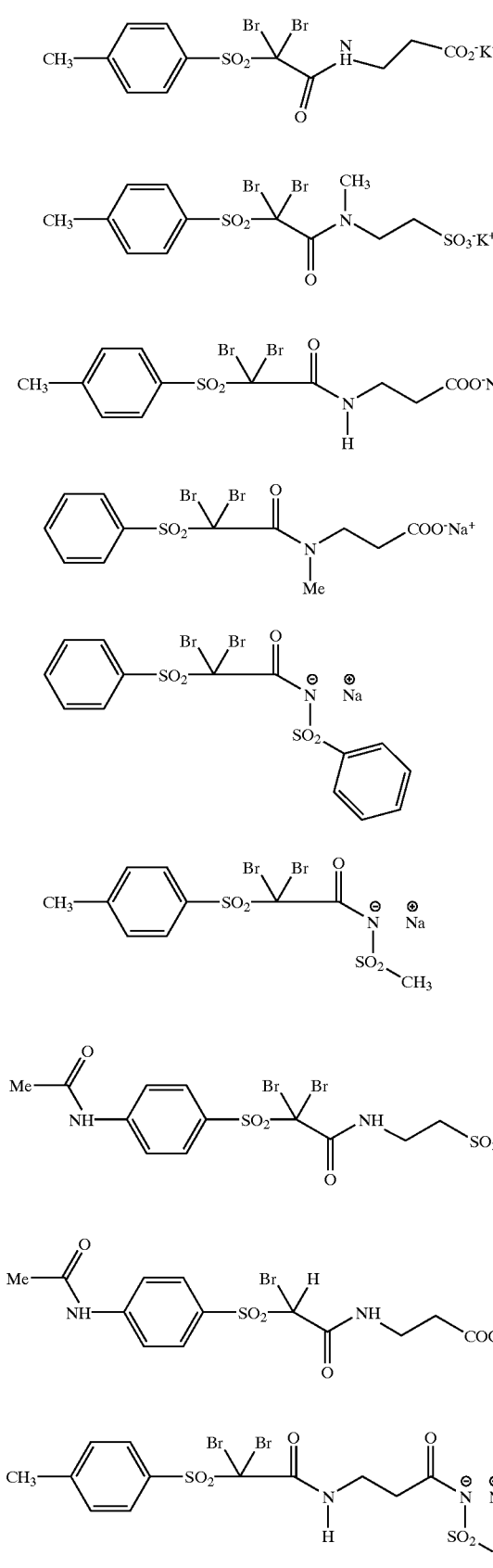
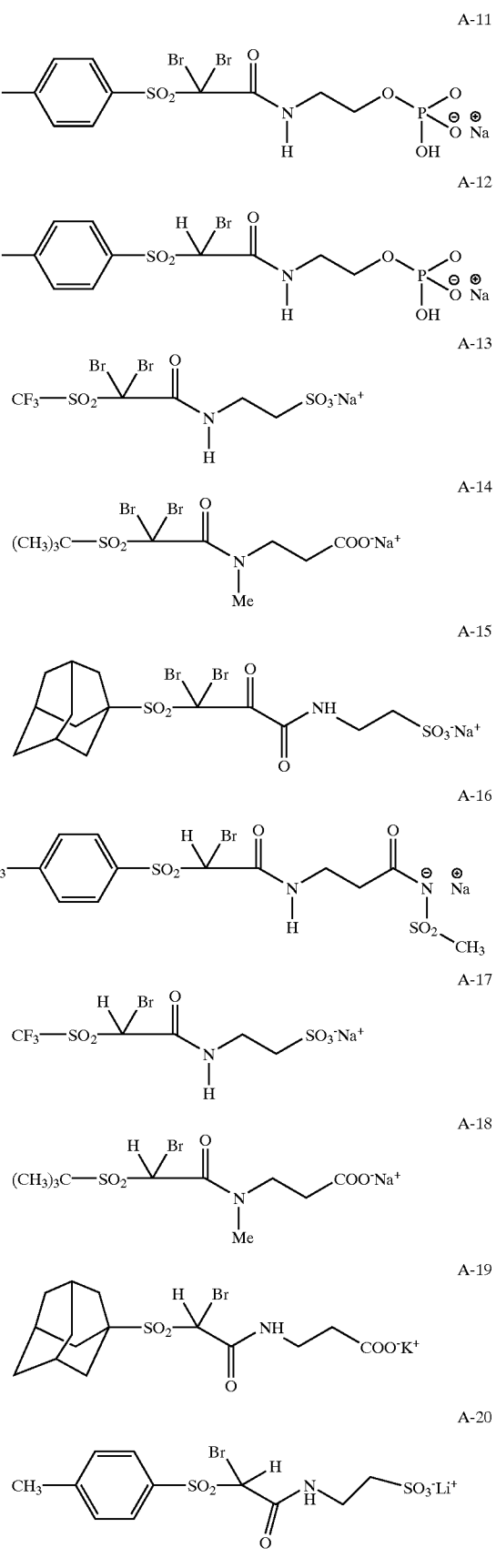

-continued
A-21
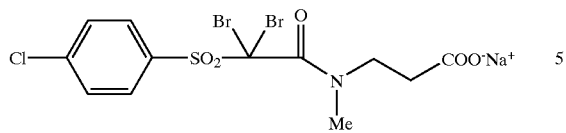
A-22
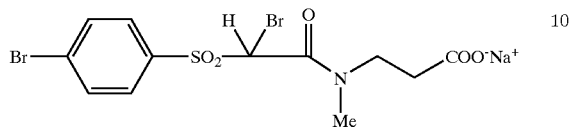
A-23
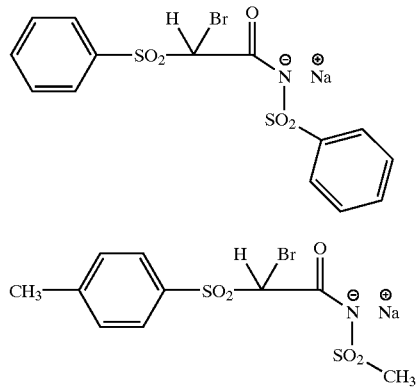
A-24
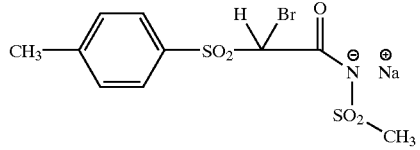
-continued
A-25
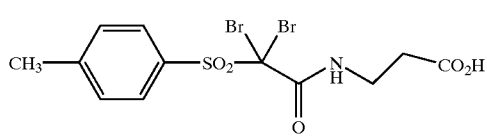
A-26
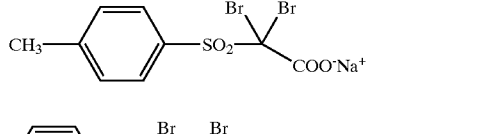
A-27
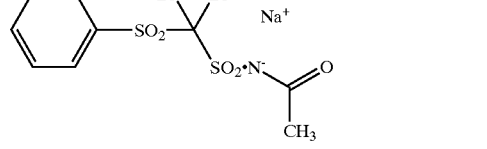
A-28
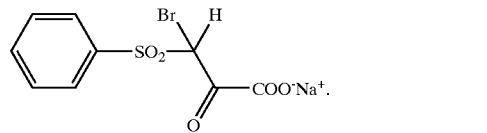
* * * * *